(12) United States Patent
Pagan et al.

(10) Patent No.: US 10,500,295 B2
(45) Date of Patent: Dec. 10, 2019

(54) APPARATUS AND METHOD FOR IRRADIATION

(71) Applicants: Jennifer Godwin Pagan, Charlotte, NC (US); Steven Franklin Pugh, Charlotte, NC (US); John Krause, Charlotte, NC (US); Oliver Lawal, Walton, KY (US); Richard Mark Simons, London (GB)

(72) Inventors: Jennifer Godwin Pagan, Charlotte, NC (US); Steven Franklin Pugh, Charlotte, NC (US); John Krause, Charlotte, NC (US); Oliver Lawal, Walton, KY (US); Richard Mark Simons, London (GB)

(73) Assignee: AQUISENSE TECHNOLOGIES LLC, Walton, KY (US)

( * ) Notice: Subject to any disclaimer, the term of this patent is extended or adjusted under 35 U.S.C. 154(b) by 0 days.

(21) Appl. No.: 16/101,890

(22) Filed: Aug. 13, 2018

(65) Prior Publication Data

US 2019/0046674 A1 Feb. 14, 2019

Related U.S. Application Data

(60) Provisional application No. 62/544,214, filed on Aug. 11, 2017.

(51) Int. Cl.
*A61L 2/10* (2006.01)
*C02F 1/32* (2006.01)

(52) U.S. Cl.
CPC .............. *A61L 2/10* (2013.01); *C02F 1/325* (2013.01); *C02F 2201/326* (2013.01);
(Continued)

(58) Field of Classification Search
CPC ...... A61L 2/10; C02F 1/325; C02F 2201/326; C02F 2201/3222; C02F 2201/3228; G21K 2201/065
(Continued)

(56) References Cited

U.S. PATENT DOCUMENTS

| 4,101,424 A | 7/1978 | Schooley et al. |
| 5,372,781 A | 12/1994 | Hallett et al. |

(Continued)

FOREIGN PATENT DOCUMENTS

| WO | 0068152 | 11/2000 |
| WO | 2010071814 | 6/2010 |
| WO | 2014107247 | 7/2014 |

OTHER PUBLICATIONS

U.S. Appl. No. 16/101,909, filed Aug. 13, 2018, Pagan, et al.
(Continued)

*Primary Examiner* — Michael Maskell
(74) *Attorney, Agent, or Firm* — Donald E. Hasse; Hasse & Nesbitt LLC (57) ABSTRACT

An apparatus and method for irradiating a fluid containing a material to be irradiated, comprising at least one irradiation chamber having at least one inlet port and outlet port, at least one fluid cooling chamber having at least one inlet port and outlet port, one or more UV radiation sources coupled to the irradiation chamber(s); and at least one heat exchange mechanism thermally coupled to the radiation source(s) and the cooling chamber(s). At least a portion of the interior surface of the cooling chamber(s) may comprise at least a portion of the exterior surface of the irradiation chamber(s) so the cooling chamber(s) is in fluid communication with the irradiation chamber(s).

34 Claims, 7 Drawing Sheets

(52) U.S. Cl.
CPC .................. *C02F 2201/3222* (2013.01); *C02F 2201/3228* (2013.01); *G21K 2201/065* (2013.01)

(58) Field of Classification Search
USPC ......... 250/428, 432 R, 435, 436, 438, 504 R
See application file for complete search history.

(56) References Cited

U.S. PATENT DOCUMENTS

| | | | |
|---|---|---|---|
| 5,372,787 A | 12/1994 | Ritter | |
| 5,753,106 A * | 5/1998 | Schenck | B01J 19/123 210/185 |
| 6,054,097 A * | 4/2000 | Mass | A61L 2/08 210/748.11 |
| 7,993,580 B2 | 8/2011 | Anderle et al. | |
| 9,265,876 B1 * | 2/2016 | Ben-Hur | A61M 1/3681 |
| 9,499,415 B2 | 11/2016 | Deguchi et al. | |
| 9,644,831 B2 | 5/2017 | Johnson, III et al. | |
| 9,855,363 B2 | 1/2018 | Stokes et al. | |
| 9,861,721 B2 | 1/2018 | Stokes et al. | |
| 9,976,953 B2 | 5/2018 | Pagan et al. | |
| 10,029,026 B2 | 7/2018 | Stokes et al. | |
| 2005/0269521 A1 | 12/2005 | Zagrobelny | |
| 2007/0295012 A1 | 12/2007 | Ho et al. | |
| 2008/0315132 A1 | 12/2008 | Platsch | |
| 2010/0296971 A1 * | 11/2010 | Gaska | A61L 2/10 422/62 |
| 2014/0014857 A1 | 1/2014 | Martinez et al. | |
| 2014/0161664 A1 | 6/2014 | Harris et al. | |
| 2017/0156378 A1 * | 6/2017 | Rimbault | A23L 2/50 |

OTHER PUBLICATIONS

International Search Report and Written Opinion dated Jan. 3, 2019 by the International Searching Authority for corresponding International Application No. PCT/US2018/046184 (11 pages).

\* cited by examiner

APPARATUS AND METHOD FOR IRRADIATION

CROSS-REFERENCE TO RELATED APPLICATION

This application claims the benefit of U.S. Provisional Application No. 62/544,214, filed on Aug. 11, 2017, the disclosure of which is incorporated by reference in its entirety.

FIELD OF THE INVENTION

The present invention relates generally to systems, apparatus and methods for disinfection of fluids by irradiation. More specifically, the invention relates to an apparatus, system and method for disinfection of fluids containing a material to be irradiated.

BACKGROUND OF THE INVENTION

The use of ultraviolet (UV) radiation for the purpose of disinfection of a fluid, including liquids and gases, is well known. The process of using ultraviolet radiation to inactivate microbial contaminants in fluids is referred to as Ultraviolet Germicidal Irradiation (UVGI). Ultraviolet radiation has also been used for oxidizing organic and inorganic materials in a fluid, termed Advance Oxidation Process (AOP), and many commercial AOP systems are in use today. Systems employing UVGI and AOP methods rely on the ability to transmit UV radiation into the fluid in a predictable manner. The dose of a UVGI system, which has units of $J/cm^2$, can be simply stated as the product of the UV irradiance in units of $W/cm^2$ and the exposure time in seconds.

Both AOP and UVGI require a UV source. For practical purposes, the output irradiance of the UV source should be maintained and decay in a predictable manner over the usage lifetime of the UV source. This enables predictions about the replacement cycle of the UV source as well as the overall performance of the system. UV disinfection systems are typically specified for a certain performance level using a variety of factors, including Reduction Equivalent Dose (RED), End of Lamp Life (EOLL), Ultraviolet Transmittance (UVT) of the fluid, and Fouling (lamp window and reactor).

Some NSF and EPA regulations require UV disinfection systems to be tested with the UV source operating at predicted EOLL optical output power. In order to adhere to the UV disinfection system performance specifications for a predicted time period, the UV source should decay in a predictable manner. There are also commercial benefits to having longer EOLL, which leads to longer system lifetimes and/or UV source replacement intervals.

There are many types of UV sources. Historically, low pressure mercury vapor lamps, medium pressure mercury vapor lamps, and amalgam lamps have been used as UV sources for disinfection applications. Other UV sources include deuterium lamps, light emitting diodes (LEDs), lasers, micro plasma sources and solid-state field effect phosphor devices. Micro plasma lamps operate on the same principle as the large gas discharge lamps but have a planar electrode generating small localized pockets of UV emission. Solid state sources such as LEDs create light in a semiconductor material though charge recombination in an active layer where charge injection is applied to an anode and cathode of the semiconductor heterostructure. All of these UV sources have different optimal operating temperatures where the UV output flux and/or the lifetime is maximized. Most gas discharge lamps are difficult to operate in very cold ambient conditions because of the lower mercury vapor pressure. Conversely, solid state sources have maximized outputs at lower ambient temperatures. For example, the output power of a low-pressure mercury lamp may peak at an ambient temperature of 40 degrees Celsius while the optical output power of a 265 nm LED displays a linear relationship with ambient temperature. The slope of the LED curve may vary by the device design, but the trend remains the same with larger optical output powers seen at lower ambient temperatures.

Many LED manufacturers specify a maximum junction temperature which should not be exceeded. The LED junction temperature is the temperature of the active layer sandwiched between the n-type and p-type semiconductor layers of the LED. Exceeding a maximum rated junction temperature may result in a decrease in the lifetime or other characteristics of the LED. In a simplified model, an LED can be represented as a series of thermal resistances. For example, a UV LED package may be a surface mount device (SMD) mounted onto a circuit board, which is itself mounted onto a heatsink or other cooling device. The heatsink may be any heat exchanger or method of cooling, such as a passive heatsink, Peltier device, active airflow, heat pipe, etc. The LED may be mounted on a variety of electrically and thermally conductive circuit boards, such as a printed circuit board (PCB), a metal core printed circuit board (MCPCB), or a chip on board (COB). Every point of connection from the junction of the LED itself to the ambient environment has a temperature associated with it. These include the junction temperature of the LED, the temperature between the LED package at the circuit board, the temperature between the circuit board and the heatsink, and the ambient temperature. At each point of connection, one can model a thermal resistance, such that $R_{JS}$ is the thermal resistance of the surface mount LED packaged, $R_{SB}$ is the thermal resistance of the circuit board, and $R_{BA}$ is the thermal resistance of the heatsink or cooling method. The LED junction temperature can be modeled as the ambient temperature added to the sum of each of the thermal resistances multiplied by the power lost to heat in the device. This relationship is shown in Equation 1.

$$T_{J(LED)} = T_{Ambient} + \Sigma_i(R_i \times P_{Heat}) \quad \text{Equation 1}$$

LEDs are unique among most UV sources in that heat is removed through the side of the chip which is electrically connected versus the side which is responsible for most of the UV emission. This is in contrast to a mercury vapor lamp, which has a thermal discharge predominantly in the same direction as light emission through a quartz sleeve, which also functions as the arc discharge tube. LEDs do not require a quartz window as they emit light directly from the active layer of the semiconductor, and the light transmits through the subsequent layers of the semiconductor to exit to the ambient. However, LEDs can be sensitive to electrostatic discharge, moisture, and ambient gases like oxygen or nitrogen which can degrade the performance of the LED electrical contacts and the semiconductor. For this reason, a quartz window is often placed on the SMD package of a LED. In UVGI systems where the LED will be protected from the fluid via a window, the window on the SMD becomes superfluous if the above environmental impacts can be mitigated. A single window over a board containing one or more LEDs can be used as the optical window for a fluid disinfection system if the LEDs are sealed between the board and the window such that the window can serve as a portion of the pressure vessel for the disinfection system and to segregate the LEDs from the fluid. Potting compounds like epoxies or silicones can be used between the board and the window to accomplish this. The potting may be undertaken in a low relative humidity environment or even purged with dry air or an inert gas to ensure any voids between the LED and window do not have undesirable moisture or gases inside. This would also increase the output power of the LED since it would pass light through one quartz window versus two. An additional benefit to this type of single window lamp package is that the LED imparts little heating to the window, in contrast to mercury vapor sources which transmit a large amount of heat to the window. Lower window temperatures have been correlated to less fouling of the window. Window fouling lowers the overall UV transmittance of the window, which in turn lowers the performance of UVGI and AOP systems. Thus, a robust product design utilizing a UV source will account for the temperature of the UV source during operation by consideration of heat transfer. By such methods the lifetime and output power of the UV source may be better controlled. In addition, methods of assembling the UV source into secondary packaging can be used to enhance the output power and lifetime of the UV source.

While the UV source is an important component in a UVGI system, it is only one component in the overall system efficiency. The system efficiency can be expressed as the product of the reactor efficiency and the UV source efficiency. It is good practice in the design of a UVGI system to maximize the exposure time, often termed the "residence time", of the fluid to the UV irradiance thereby maximizing the dose seen by the fluid. The reactor efficiency is a combination of the residence time efficiency and the optical efficiency. The optical efficiency of the reactor is a measure of how effectively the reactor uses photons from the UV source to increase the probability that a microbial contaminant in the fluid will absorb a photon. One method of increasing this probability is to use reflective materials in the reactor such that photons from the UV source may be reflected if they are not absorbed during their initial pass inside the reactor. If there are few absorbers in the fluid and the reflectivity of the material in the reactor is high, the photons may be reflected multiple times inside the reactor.

U.S. Patent Application Publications 2012/0318749 A1, 2014/0161664 A1, and 2014/0240695 A1, all incorporated herein by reference, disclose various apparatus, materials and methods useful herein for disinfection of fluids by irradiation. However, what is still needed in the art is an improved apparatus and method for irradiation that provides good system efficiency, incorporates adequate thermal management, and can be used with a variety of housings or flow cells, all while maintaining a compact footprint.

SUMMARY OF THE INVENTION

In one embodiment, the invention relates to an irradiation apparatus comprising: at least one irradiation chamber for a fluid containing a material to be irradiated, said chamber having at least one inlet port for fluid flow into the chamber and at least one outlet port for fluid flow out of the chamber; at least one cooling chamber having at least one inlet port for fluid flow into the chamber and at least one outlet port for fluid flow out of the chamber; one or more UV radiation sources coupled to the at least one irradiation chamber; and at least one heat exchange mechanism thermally coupled to the one or more radiation sources and to the at least one cooling chamber; wherein at least a portion of the interior surface of the at least one cooling chamber comprises at least a portion of the exterior surface of the at least one irradiation chamber, and the at least one cooling chamber is in fluid communication with the at least one irradiation chamber.

In another embodiment, the invention relates to a method for irradiating a fluid containing a material to be irradiated disposed in an irradiation chamber, the irradiation method comprising (1) providing an irradiation apparatus comprising: at least one irradiation chamber for a fluid containing a material to be irradiated, said chamber having at least one inlet port for fluid flow into the chamber and at least one outlet port for fluid flow out of the chamber; at least one cooling chamber having at least one inlet port for fluid flow into the chamber and at least one outlet port for fluid flow out of the chamber; one or more UV radiation sources coupled to the at least one irradiation chamber; and at least one heat exchange mechanism thermally coupled to the one or more radiation sources and to the at least one cooling chamber; wherein at least a portion of the interior surface of the at least one cooling chamber comprises at least a portion of the exterior surface of the at least one irradiation chamber, and the at least one cooling chamber is in fluid communication with the at least one irradiation chamber, and (2) irradiating a fluid containing a material to be irradiated using said irradiating apparatus.

In another embodiment, the invention relates to an irradiation apparatus and method comprising: at least one irradiation chamber for a fluid containing a material to be irradiated, said chamber having at least one inlet port for fluid flow into the chamber and at least one outlet port for fluid flow out of the chamber; at least one cooling chamber having at least one inlet port for fluid flow into the chamber and at least one outlet port for fluid flow out of the chamber; one or more UV radiation sources coupled to the at least one irradiation chamber; and at least one heat exchange mechanism thermally coupled to the one or more radiation sources and to the at least one cooling chamber.

BRIEF DESCRIPTION OF THE DRAWINGS

The invention is illustrated and described herein with reference to the various drawings, in which like reference numbers are used to denote like apparatus components, as appropriate, and in which.

DETAILED DESCRIPTION OF THE INVENTION

The present invention provides an improved UV irradiation apparatus, disinfection system and method which utilizes a secondary reactor chamber to cool the UV source, and in one embodiment, to also increase the exposure time of the fluid containing a material to be irradiated inside the system. The UV source directly irradiates a primary reactor chamber with interior surfaces typically made of material which principally reflects the UV radiation and minimally transmits the UV radiation through the material. In one embodiment, at least a portion of the interior surface of the secondary reactor comprises at least a portion of the exterior surface of the primary reactor chamber. The secondary reactor chamber thus receives the fraction of UV radiation transmitted through the material of the primary reactor. In one embodiment, the secondary, cooling chamber is in fluid communication with the primary, irradiation chamber. Cooling of the UV source is accomplished via at least one heat exchange mechanism thermally coupled to the UV source and to the fluid in the secondary, cooling chamber.

In another embodiment, the UV irradiation apparatus, disinfection system and method are designed such that a portion of radiation from the one or more radiation sources is transmitted from the irradiation chamber into one or more secondary chambers, including but not limited to a cooling chamber or outlet conduit, such that the radiation disposed to surfaces of the one or more secondary chambers provides a disinfection effect to inhibit the propagation of microbiological contamination. Microbial attachment to surfaces of the irradiation apparatus, hereinafter referred to as "biofilm" formation, may increase risk to health due to possible transfer of such contaminants to a fluid flowing across such surfaces. The inhibition of biofilm within the disinfection system is desirable since the process of UV irradiation does not impart a residual biocide to the fluid treated. Fouling of the irradiation apparatus and disinfection system is most critically avoided in downstream regions of the apparatus and system, including but not limited to the 'last mile', being later within the process chain than the principle irradiation chamber. In one embodiment, a small portion of the radiation emitted by the UV source may be redirected to irradiate surfaces of the treatment apparatus and system. Since the fluid-contact surfaces of the reactor are static, the irradiation period of any segment is equal to the total period for which the UV source is emitting. Thus, far lower irradiances are required to achieve biofilm inhibition than would be necessary for transient irradiation, such as for a fluid passing through a reactor chamber. By requiring low irradiance and relatively low UV power, a small fraction of the power emitted by the source can be scavenged for biofilm inhibition without significantly impacting the fluid disinfection performance of the reactor. Thus, a portion of the radiation from the one or more radiation sources can be transmitted to surfaces of the one or more secondary chambers to inhibit biofilm formation thereon.

In one embodiment of the invention, the apparatus has two three-dimensional chambers, each of which has at least one inlet port and at least one outlet port for the flow of fluid into and out of the chambers. A UV radiation source provides radiation to the interior of one of the chambers, the irradiation chamber. The radiation source has a thermal connection to the other chamber, the cooling chamber. This thermal connection is between the backside and/or frontside of a heat exchange mechanism connected to the UV source and the fluid in the cooling chamber. The two chambers are in fluidic connection where the inlet of one of the chambers is the outlet for the other chamber. The irradiation chamber is typically constructed from a material which principally reflects the UV radiation from the UV source and minimally transmits the UV radiation. The cooling chamber has at least a portion of its chamber interior comprised of the exterior of the irradiation chamber. UV radiation transmitted through the material of the irradiation chamber thus serves as the UV source for the cooling chamber. This increases the exposure time of the fluid to the UV radiation and increases the dose seen by the fluid. Moreover, the radiation transmitted to surfaces of the cooling chamber inhibits biofilm formation thereon.

The UV radiation source (or a plurality of UV radiation sources) may comprise one or more UV-C radiation sources, or a combination thereof. The UV radiation source (or plurality of UV radiation sources) is typically coupled to a support structure in or on a wall of the irradiation chamber or the cooling chamber. The support structure holds the UV radiation source(s), which may be UV-C radiation source(s), such that they selectively direct UV radiation into the interior of an irradiation chamber in which a material to be irradiated is selectively disposed. Peak wavelengths may be (dynamically) selected and/or adjusted, and a plurality of wavelengths may be utilized such that the action spectrum of a given organism can be targeted, thus improving disinfection efficiency. For example, one or more wavelengths of the one more UV radiation sources may be selected based on an identification of a contaminant in the material to be irradiated. The one or more UV radiation sources may deliver one or more wavelengths, or a combination of wavelengths, to the material to be irradiated. The wavelengths may induce fluorescence in the material to be irradiated thereby allowing for the identification of the contaminant in the material to be irradiated. Optionally, the material to be irradiated may be disposed adjacent to an n-type single crystalline semiconductor to generate hydrogen peroxide at the semiconductor surface through bandgap electric photo-excitation for disinfection. Heat is managed, and optionally recuperated, using a heat exchange mechanism, such as one or more of a thermoelectric cooling device, a vapor chamber, a heatsink, a heat dissipation structure, a fan, a thermal transfer material, a material thermally coupled to a fluid, and a cooling coating, disposed substantially adjacent to the UV radiation source(s). In one embodiment, the heat exchange mechanism is a heatsink or a thermal transfer material, or combinations thereof. The irradiation apparatus may be made moisture resistant using a moisture seal and desiccant coupled to and/or disposed within the support structure. The irradiation assembly can include a monitoring/detection mechanism and control circuitry for dynamically controlling the delivery of UV radiation to the material to be irradiated based on flow rate, water quality, user input, or other operating conditions. Finally, associated performance data may be stored in an onboard or external data storage unit.

In various embodiments of the invention, a modular semiconductor UV LED mounting configuration may be provided including a UV radiation source package containing a single LED or multiple LED "dice" arranged in a matrix or array. The LED dice can be selected to provide multiple wavelengths in both the UV and visible radiation spectrum from about 200 nm to about 800 nm. In one exemplary embodiment, the matrix or array includes LED dice emitting wavelengths in the range of about 200-320 nm in order to saturate the absorption mechanism of nucleocapsids (with peak emission centered at around 280 nm), and at the same time to target the peak absorption of nucleic acid with its peak emission wavelength spanning about 250-280 nm. In another exemplary embodiment, with the intention of mimicking the optical output spectrum of low or medium pressure Hg-based UV lamps used to target various bacteria and viruses, the matrix or array of LED dice utilizes multiple wavelengths, including at least one of about 240-260 nm, about 260-344 nm, about 350-380 nm, about 400-450 nm, or about 500-600 nm. A further exemplary embodiment is a matrix or array of LED dice emitting germicidal wavelengths ranging from about 250 nm to 300 nm in conjunction with LED dice emitting wavelengths in the range of about 350 nm to 400 nm to enable photocatalytic oxidation of pathogens or pollutants in water in proximity of crystalline films of n-type semiconductors, such as $TiO_2$, $NiO$, or $SnO_2$. A still further exemplary embodiment is a modular mounting configuration containing multiple LED dice emitting about 250-320 nm and about 320-400 nm wavelengths arranged in a matrix or array to enable the fluorescence spectra of NADH, and tryptophan, of particles with biological origin. In another exemplary embodiment, a commercially available SETi UV Clean™ LED package is used. Individual LED dice or a single die bonded to a thermally conductive metal core circuit board (MCPCB), such as those available from The Bergquist Company™, may also be used.

The LED package may be connected to a heat dissipation sink, which is in turn configured to mount to a window port of the irradiation chamber. The mounting face of the module may possess a seal or gasket, which encloses the LED package along with a desiccant, thus reducing condensing moisture. The heatsink may be round, square, or another suitable shape. Heat from the LEDs is optionally conducted by the aid of a thermoelectric cooler or other means to the heatsink, which is optionally cooled by forced air. The LED package may be electrically connected to control and power circuitry, which is included as part of the replaceable module. Circuitry is included within the replaceable module in order to provide telemetric data and track information, such as operating temperature and run time.

A packaged UV LED, or a matrix or array of multiple UV LEDs, may be attached to the heatsink. Multiple UV wavelengths can be used to optimize the effect on specific microorganisms. Backside heat extraction may be aided by thermoelectric cooling (TEC) and/or a vapor chamber. Additionally, the UV LED package may be topside cooled by conduction through a highly thermally conductive overlayer, such as silicone polymer impregnated with diamond nanoparticles, which may have a single crystalline structure.

The surface of the metal portion of the heatsink and UV radiation emitting housing may be flat for mounting the LED and accessory dies or packages; or optionally recessed in order to provide a concave reflective structure for the LEDs and/or to provide means for attachment. The heatsink may be attached to the irradiation apparatus by a variety of methods, including, but not limited to, contact adhesion, spring pins, clamps, clips that swivel, screws, by screwing in an exemplary embodiment of the heatsink with a rounded bezel that has threads cut into it, or by twisting in an exemplary embodiment of the heatsink with a rounded bezel which connects by means of a bayonet connector.

Components for the electrical and/or electronic control of the UV radiation source may optionally be included within the sealed unit as previously described, such that they may act upon the UV radiation source whilst maintaining protection from the external environment through such hermiticity, the use of desiccants, or a combination thereof as previously described. Further, the co-location of these components onto the MCPCB, or otherwise, and subsequent thermal union to the heat exchange mechanism may be used to extract heat generated by, for example, power conversion components. Additionally, these electrical and/or electronic components may include sensors by which the operating conditions and status of the UV radiation source may be determined, including but not limited to a photodiode, thermocouple, thermistor, acoustic sensor, hall probe, current probe, etc.

The radiation emitter module may be a user replaceable unit, optionally including attached electronics and desiccating materials in order to combat moisture and humidity. Attached electronics can include an individual identification number and telemetry tracking, as well as an interconnect for easy disconnect from a larger system.

Cooling of the LED package may be assisted by a TEC or vapor chamber situated between the LED package and the heatsink. The TEC may take the form of a single TEC, or multiple modules situated to provide contact around irregular package geometry, such as a through-hole design. Furthermore, electro-thermal modules may be included to harvest energy from the waste heat created.

The UV radiation may be transmitted from the LED dice through a transmissive window, polymer, air, and/or aperture into the irradiation chamber. The transmissive window has a transmission spectrum appropriate for the choice of LEDs used, for example the UV-C range.

Figure 1:
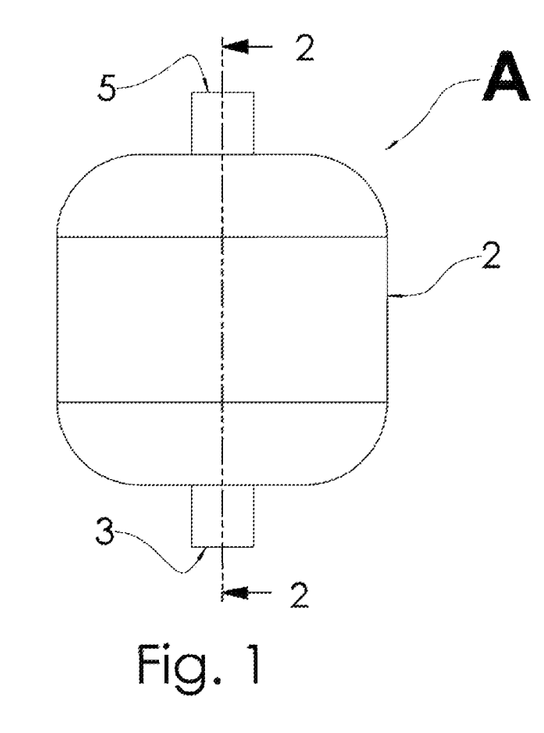
FIG. 1 is a planar side view illustrating one exemplary embodiment of the irradiation apparatus of the invention.
Figure 2:
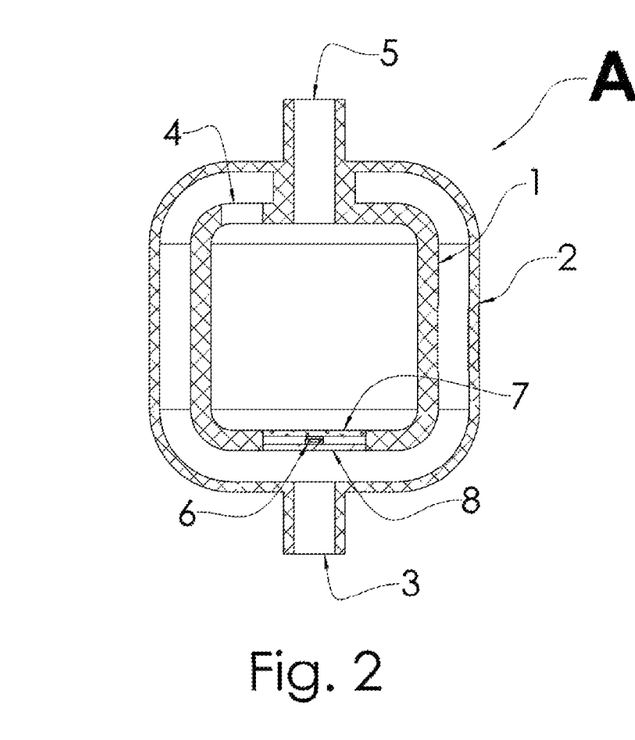
FIG. 2 is a section view of the apparatus of FIG. 1 taken along line 2-2.

Referring now to FIGS. 1 and 2, in one exemplary embodiment of the invention, the irradiation apparatus A includes two three-dimensional chambers 1 and 2, each having an inlet port and an outlet port for the flow of a fluid into and out of the chambers. Irradiation chamber 1 has inlet port 4 for fluid flow into the chamber and outlet port 5 for fluid flow out of the chamber. Cooling chamber 2 has inlet port 3 for fluid flow into the chamber and outlet port 4 for fluid flow out of the chamber. Cooling chamber 2 and irradiation chamber 1 are in fluidic connection and in fluid communication, with port 4 functioning as both the outlet port for the cooling chamber and the inlet port for the irradiation chamber. A UV radiation source 6 provides radiation to the interior of irradiation chamber 1. The radiation source has a thermal connection to the cooling chamber 2. This thermal connection is between the backside and/or frontside of at least one heat exchange mechanism thermally connected or coupled to the radiation source and to the fluid in the cooling chamber. In one embodiment, the heat exchange mechanism is heatsink 8. A single, quartz optical window 7 is placed over the UV radiation source 6 to protect it from fluid in the irradiation chamber 1. The UV radiation source is sealed between the heat exchange mechanism and the window such that the window serves as a portion of the pressure vessel for the disinfection system and to segregate the UV radiation source from the fluid in the irradiation chamber.

Irradiation chamber 1 is typically constructed from a material which principally reflects the UV radiation from the UV source and minimally transmits the UV radiation. At least a portion of the interior surface of the cooling chamber 2 comprises at least a portion of the exterior surface of the irradiation chamber 1. The interior surface of the cooling chamber (or chambers) typically comprises at least a substantial portion of the exterior surface of the irradiation chamber(s), more typically substantially all of the exterior surface of the irradiation chamber(s), such that the cooling chamber(s) substantially or completely enclose the irradiation chamber(s). In one embodiment, the total exterior surface of the one or more irradiation chambers in the irradiation apparatus is at least about 20%, typically at least about 30%, more typically at least about 40%, of the total interior surface of the one or more cooling chambers in the irradiation apparatus. The UV radiation transmitted through the material of chamber 1 serves as the UV source for cooling chamber 2. Thus, the dose, $D_m$, received by any particle flowing through the two chamber system described can be expressed by the following equation $$D_m = t_A \varphi_A + t_B \varphi_B$$

where $t_A$ and $t_B$ are the residence times of the particle in chambers 1 and 2, respectively, and $\varphi_A$ and $\varphi_B$ are the radiometric flux seen by the particle in chambers 1 and 2, respectively.

In another embodiment, the UV source is a LED which is in electrical and thermal connection to a thermal transfer material, such as a metal core printed circuit board (MCPCB), printed circuit board (PCB) or other dielectric material. The thermal transfer material is in direct contact with the fluid in cooling chamber 2, providing a thermal path between the LED and the fluid. In this case, the fluid will provide cooling to the LED if the fluid, e.g., water, temperature is lower than the junction temperature. The thermal transfer material functions as a heat exchange mechanism thermally connected or coupled to the radiation source and to the fluid in the cooling chamber.

In another embodiment, the UV source is a LED which is in electrical and thermal connection to a thermal transfer material, such as a metal core printed circuit board (MCPCB), printed circuit board (PCB) or other dielectric material, which is in contact with a separate, second thermal transfer material in direct contact with the fluid in the irradiation chamber 1, providing a thermal path between the LED and the fluid. In this case, the fluid will provide cooling to the LED if the fluid, e.g., water, temperature is lower than the junction temperature. The second thermal transfer material may be a metal, dielectric, semiconductor, plastic or any other thermally conductive material. The thermal transfer material functions as a heat exchange mechanism thermally connected or coupled to the radiation source and to the fluid in the cooling chamber.

In another embodiment, the cooling chamber 2 also serves to increase the structural integrity of the combined system shown in FIGS. 1-2 such that the pressure rating of the entire system (chambers 1 and 2) is increased. For example, the cooling chamber may be made of a material having a higher tensile strength than the material used to make the irradiation chamber.

In another embodiment, optical coupling between the irradiation chamber and the one or more cooling chambers or other secondary chambers may be accomplished via one or more portholes through the interior of the irradiation chamber to allow for UV radiation to enter the cooling or other secondary chambers from the irradiation chamber. The porthole(s) may also be in fluidic connection to the cooling chamber(s) and increase fluid communication between the irradiation and secondary chambers. Radiation transmitted through the porthole(s) to surfaces of the cooling or other secondary chambers inhibits biofilm formation on their surfaces and possible microbial contamination in downstream regions of the apparatus. Thus, a portion of the fluidic outlet structure of the irradiation apparatus may be optically coupled to the irradiation chamber, either through direct illumination through one or more portholes or other openings in the irradiation chamber or via partial transmission through the material of the chamber, such that the surfaces of the outlet structure are irradiated to inhibit biofilm formation thereon. The UV radiation may be used as a biofilm inhibitor within an integrated UV disinfection apparatus, system and method. This may include intelligent control of the apparatus, system and method with periodic "on cycles" during periods of non-use, such that a constant bacteriostatic effect may be imparted. In one embodiment, optical coupling between the irradiation chamber 1 and cooling chamber 2 may be accomplished via at least one small porthole through the interior of chamber 1 to allow for UV radiation to enter chamber 2 from chamber 1. The porthole(s) may also be in fluidic connection to chamber 2 and increase fluid communication between chambers 1 and 2. The radiation transmitted to surfaces of chamber 2 through the at least one small porthole and via partial transmission through the material of chamber 1 also inhibits biofilm formation on surfaces of chamber 2 and possible microbial contamination in downstream regions of the apparatus.

In another embodiment of the invention, the UV source transmits radiation to an irradiation chamber and is thermally coupled to a cooling chamber that is structurally distinct from the irradiation chamber. In the embodiment shown in FIGS. 3 and 4, the irradiation apparatus B includes two three-dimensional chambers 9 and 10, each having an inlet port and an outlet port for the flow of a fluid into and out of the chambers. Irradiation chamber 9 has inlet port 12 for fluid flow into the chamber and outlet port 13 for fluid flow out of the chamber. Cooling chamber 10 has inlet port 11 for fluid flow into the chamber and outlet port 17 for fluid flow out of the chamber. However, cooling chamber 10 and irradiation chamber 9 are structurally distinct and not in fluidic connection or fluid communication. A UV radiation source 14 provides radiation to the interior of irradiation chamber 9. The radiation source has a thermal connection to the cooling chamber 10. This thermal connection is between the backside and/or frontside of at least one heat exchange mechanism thermally connected or coupled to the radiation source and to the fluid in the cooling chamber. In one embodiment, the heat exchange mechanism is heatsink 16. A single, quartz optical window 15 is placed over the UV radiation source 14 to protect it from fluid in the irradiation chamber 9. The UV radiation source is sealed between the heat exchange mechanism and the window such that the window serves as a portion of the pressure vessel for the disinfection system and to segregate the UV radiation source from the fluid in the irradiation chamber. Irradiation chamber 9 is constructed from a material which principally reflects the UV radiation from the UV source and minimally transmits the UV radiation.

Figure 3:
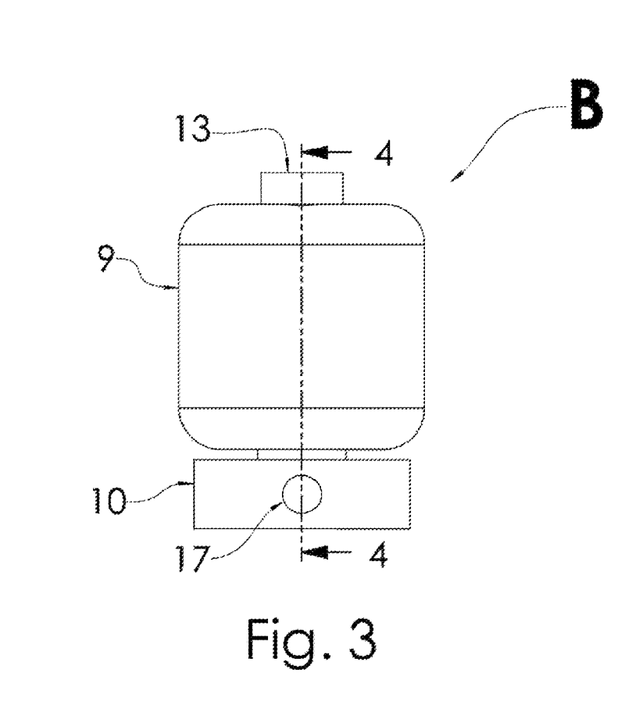
FIG. 3 is a planar side view illustrating another apparatus of the invention.
Figure 4:
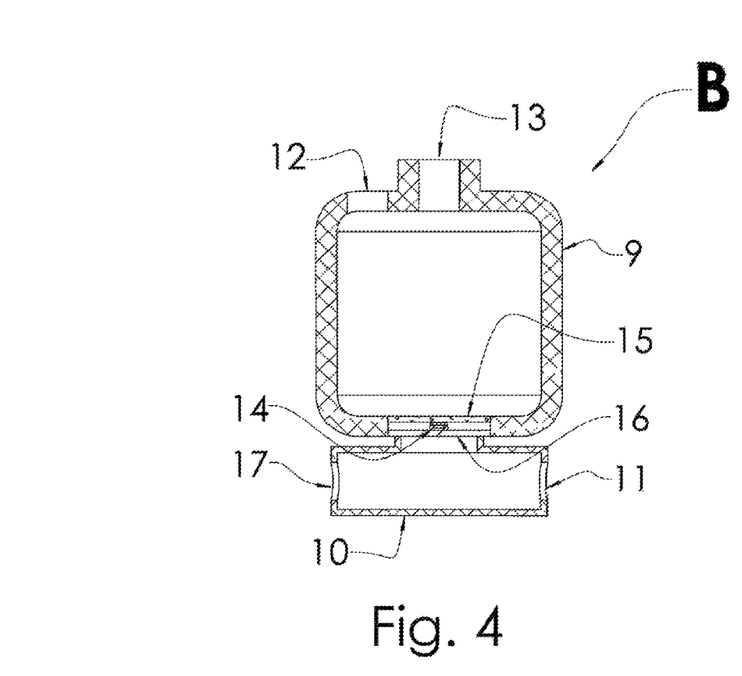
FIG. 4 is a section view of the apparatus of FIG. 3 taken along line 4-4.

In another embodiment, the irradiation chamber 9 and the cooling chamber 10 are dependent upon a single rigid frame for structural stability. The partition between the chambers is accomplished with a material that is primarily non-structural. In another embodiment, the partition between the chambers is semi-permeable, allowing for fluidic flux between chambers.

In another embodiment, the UV radiation source is thermally connected to a thermal transfer material that is partially or entirely coupled to or mounted inside the interior of the irradiation chamber. The thermal transfer material provides conductive heat transfer from the UV source to the fluid in the irradiation chamber via the interior of the chamber. In one embodiment, the UV source is an LED which is in electrical and thermal connection to the thermal transfer material, such as a metal core printed circuit board (MCPCB), printed circuit board (PCB) or other dielectric material. The thermal transfer material is in direct contact with the fluid in the irradiation chamber providing a thermal path between the LED and the fluid. In this case, the fluid will provide cooling to the LED if the fluid, e.g., water, temperature is lower than the junction temperature. The thermal transfer material functions as a heat exchange mechanism thermally connected or coupled to the radiation source and to the fluid in the cooling chamber.

Figure 5:
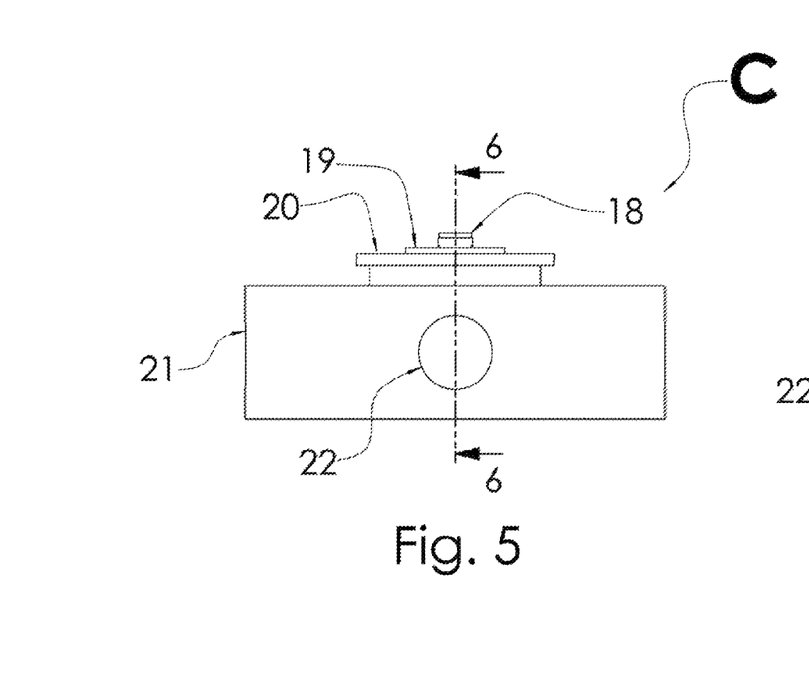
FIG. 5 is a planar side view illustrating a portion of another apparatus of the invention.
Figure 6:
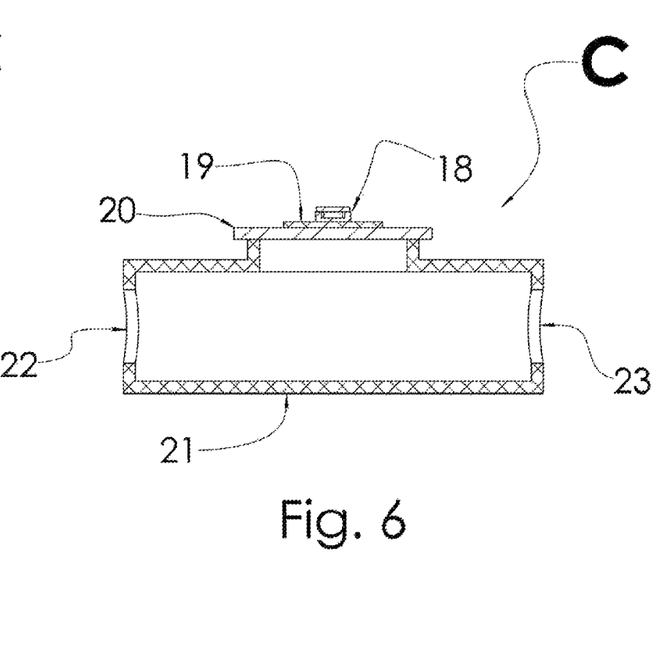
FIG. 6 is a section view of the portion of the apparatus of FIG. 5 taken along line 6-6.

In another embodiment, the UV source is an LED which is in electrical and thermal connection to the thermal transfer material, such as a metal core printed circuit board (MCPCB), printed circuit board (PCB) or other dielectric material, which is in contact with a separate thermal transfer material in direct contact with the fluid in the irradiation chamber, providing a thermal path between the LED and the fluid. In this case, the fluid will provide cooling to the LED if the fluid, e.g., water, temperature is lower than the junction temperature. The thermal transfer material may be a metal, dielectric, semiconductor, plastic or any other thermally conductive material. The thermal transfer material functions as a heat exchange mechanism thermally connected or coupled to the radiation source and to the fluid in the cooling chamber. FIGS. 5 and 6 illustrate a portion of one such apparatus of the invention. In one example, apparatus B shown in FIGS. 3 and 4 can be modified to include the apparatus C cooling chamber 21, UV radiation source 18, and heat exchange mechanisms 19 and 20 shown in FIGS. 5 and 6 instead of the cooling chamber, UV radiation source and heat exchange mechanism in FIGS. 3 and 4. Cooling chamber 21 has inlet port 22 for fluid flow into the chamber and outlet port 23 for fluid flow out of the chamber. UV radiation source 18 provides radiation to the interior of the irradiation chamber. The UV source is in electrical and thermal connection with thermal transfer material 19, such as a metal, dielectric, semiconductor, plastic or any other thermally conductive material, e.g, a metal core printed circuit board (MCPCB), printed circuit board (PCB) or other dielectric material. Thermal transfer material 19 is in contact with a separate heat exchange mechanism 20, such as a heatsink or another thermal transfer material as described above, which is in direct contact with the fluid in the irradiation chamber providing a thermal path between the UV radiation source and the fluid. In this case, the fluid will provide cooling to the UV radiation source if the fluid, e.g., water, temperature is lower than the junction temperature. The radiation source also has a thermal connection to the cooling chamber 21 via the heat exchange mechanisms 19 and 20 thermally connected or coupled to the radiation source and to the fluid in the cooling chamber. In another embodiment, the UV source 18 also provides UV radiation to the thermal transfer material 19.

Figure 7:
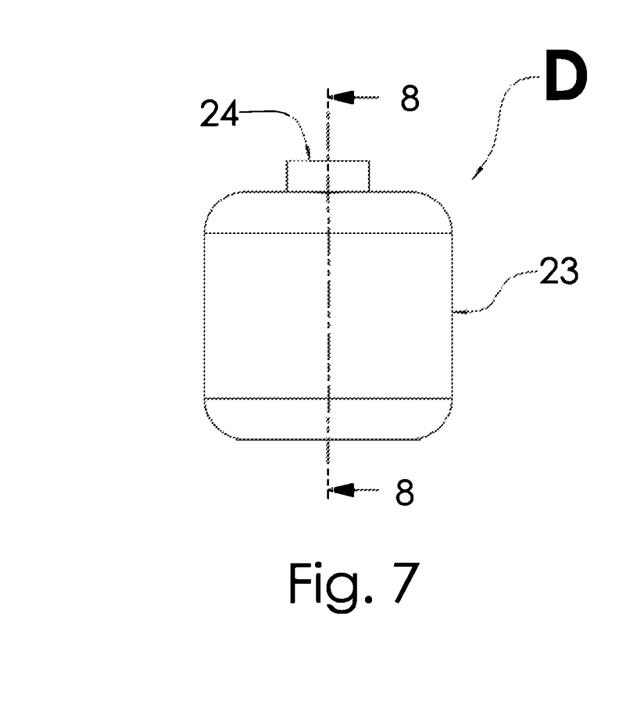
FIG. 7 is a planar side view illustrating another apparatus of the invention.
Figure 8:
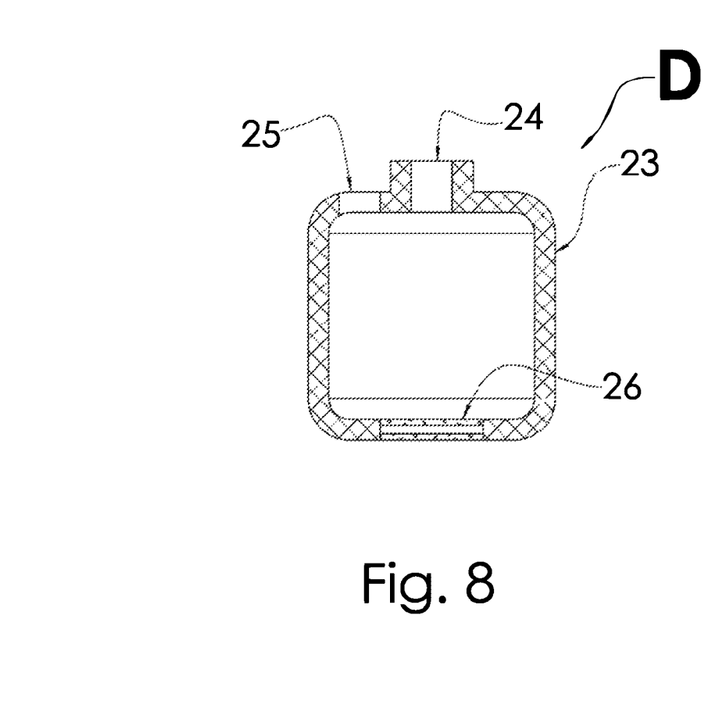
FIG. 8 is a section view of the apparatus of FIG. 7 taken along line 8-8.

In another embodiment, the UV source is a micro plasma lamp which is in direct contact with the fluid in the reactor irradiation chamber providing a direct thermal path between the lamp and the fluid. In this case, the fluid will provide cooling to the lamp. In the embodiment shown in FIGS. 7 and 8, the irradiation apparatus D includes a three-dimensional irradiation chamber 23 having an inlet port 24 and an outlet port 25 for the flow of a fluid into and out of the chamber. A micro plasma lamp UV radiation source 26 provides radiation to the interior of irradiation chamber 23. Because the micro plasma lamp is in direct contact with the fluid in chamber 23, it provides a direct thermal path between the lamp and the fluid, thereby cooling the lamp. In one embodiment, the micro plasma lamp is in thermal connection with a thermal transfer material which is in direct contact with the fluid in the irradiation chamber, providing a thermal path between the lamp and the fluid. The thermal transfer material may be a metal, dielectric, semiconductor, plastic or any other thermally conductive material. The thermal transfer material may reflect a portion of the UV radiation from the lamp. In another embodiment, the thermal transfer material is in contact with a separate thermal transfer material which is in direct contact with the fluid in the irradiation chamber, providing a thermal path between the lamp and the fluid. In these cases, the fluid will provide cooling to the lamp. As such, the embodiment shown in FIGS. 7 and 8 may be used as an irradiation chamber in the other irradiation apparatus shown and described herein.

In another embodiment, the invention provides a plurality of UV radiation sources and a plurality of irradiation chambers, each with at least one inlet and one outlet port. Each UV radiation source is primarily optically coupled to a single irradiation chamber. All irradiation chambers are fluidically coupled to a single cooling chamber such that all fluid that passes through any irradiation chamber also passes through the cooling chamber. In this way, the fluidic flux through the cooling chamber is equal to the sum of fluidic fluxes through all the irradiation chambers. In addition, all UV sources are thermally coupled to the fluidic flux via the interior of the cooling chamber.

In another embodiment, the invention provides a plurality of UV radiation sources and a plurality of irradiation chambers, each with at least one inlet and one outlet port. Each UV radiation source is primarily optically coupled to a single irradiation chamber. All of the UV radiation sources are thermally coupled to the single cooling chamber. One or more of the irradiation chambers is in fluidic connection, where the outlet of one chamber is the inlet for another chamber.

In another embodiment, the invention provides a plurality of UV radiation sources and a plurality of irradiation chambers each with at least one inlet and one outlet port. Each UV radiation source is primarily optically coupled to a single irradiation chamber. All the UV radiation sources are thermally coupled to the single cooling chamber. One or more of the irradiation chambers are in fluidic connection, where the outlet of one chamber is the inlet for another chamber. In addition, the cooling chamber is in fluid connection to one or more of the irradiation chambers, where the outlet of the cooling chamber is the inlet of one or more of the irradiation chambers.

In the embodiments described above, the plurality of irradiation chambers are fluidically coupled to a single cooling chamber such that all fluid that passes through any irradiation chamber also passes through the cooling chamber. Just as multiple irradiation chambers may be fluidically coupled to a single cooling chamber, forming a single unit, sets of these individual units may be arrayed in parallel or series combinations where the inlet to each unit is composed of a fraction of the total inlet flow (parallel case) or the entire flow (series case), or a blend of series and parallel configurations of each unit.

Figure 9:
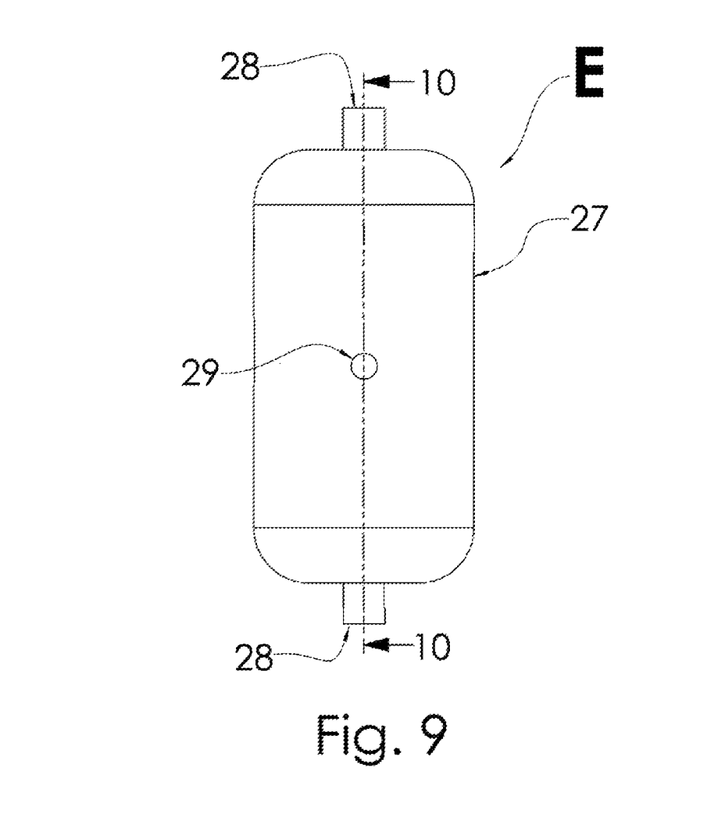
FIG. 9 is a planar side view illustrating another apparatus of the invention.
Figure 10:
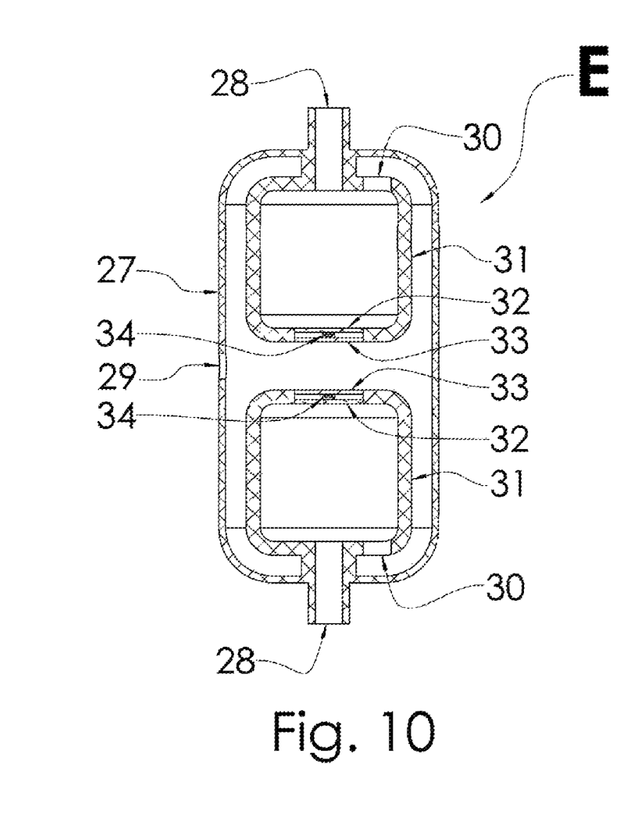
FIG. 10 is a section view of the apparatus of FIG. 9 taken along line 10-10.

In the embodiment shown in FIGS. 9 and 10, irradiation apparatus E includes three three-dimensional chambers, two irradiation chambers 31 and cooling chamber 27. Each chamber has an inlet port and an outlet port for the flow of fluid into and out of the chambers. Each irradiation chamber 31 has an inlet port 30 for fluid flow into the chamber and an outlet port 28 for fluid flow out of the chamber. Cooling chamber 27 has inlet port 29 for fluid flow into the chamber and two outlet ports 30 for fluid flow out of the chamber. Cooling chamber 27 and irradiation chambers 31 are in fluidic connection and fluid communication, with ports 30 functioning as both the outlet ports for the cooling chamber and the inlet ports for the irradiation chambers. A UV radiation sources 34 provides radiation to the interior of irradiation chambers 31. The radiation sources have a thermal connection to the cooling chamber 27. This thermal connection is between the backside and/or frontside of at least one heat exchange mechanism thermally connected or coupled to each radiation source and to the fluid in the cooling chamber. In one embodiment, the heat exchange mechanism is via each heatsink 33. A single, quartz optical window 32 is placed over each UV radiation source 34 to protect it from fluid in its irradiation chamber. The UV radiation source is sealed between the heat exchange mechanism and the window such that the window serves as a portion of the pressure vessel for the disinfection system and to segregate the UV radiation source from the fluid in the irradiation chamber. As described above, each UV radiation source 34 is primarily optically coupled to a single irradiation chamber 31. All the UV radiation sources are thermally coupled to the single cooling chamber 27. The irradiation chambers 31 are in fluidic connection and fluid communication with the cooling chamber 27 and with each other since the outlets 30 of the cooling chamber are the inlets for the irradiation chambers.

In another embodiment, the transfer of heat from the UV source to the fluidic flux is accomplished via conductive heat transfer through a nominally flat surface that is incorporated into the surface of a chamber, in thermal contact with the fluidic flux within that chamber. For example, in the embodiments shown in FIGS. 2 and 10, the transfer of heat from the UV source to the fluid in the cooling chamber is accomplished via conductive heat transfer through a nominally flat surface of the heatsink incorporated into the outer surface of the irradiation chamber and the inner surface of the cooling chamber, which is in thermal contact with the fluidic flux within the cooling chamber.

In another embodiment, the transfer of heat from the UV source to the fluidic flux is accomplished via conductive heat transfer through a porous structure placed in the flow path of some or all of the fluidic flux. The porous structure may be designed such that the surface area is maximized to provide for efficient conductive heat transfer to the fluidic flux. The porous structure used for maximizing conductive heat transfer may also promote turbulent mixing of the fluidic flux and/or laminar flow characteristics in the fluidic flux.

In one embodiment of the invention, two three-dimensional chambers have at least one inlet and at least one outlet port for the flow of a fluid into and out of the chamber. The UV source is a planar source such as a micro plasma lamp, emitting UV radiation from both sides. The UV source is situated between the irradiation chamber and the cooling chamber and provides radiation to both chambers. In one embodiment, the two chambers are in fluidic connection, where the inlet of one of the chambers is the outlet for the other chamber. In another embodiment, each side of the planar UV source serves as a portion of the sidewall of each chamber.

Figure 11:
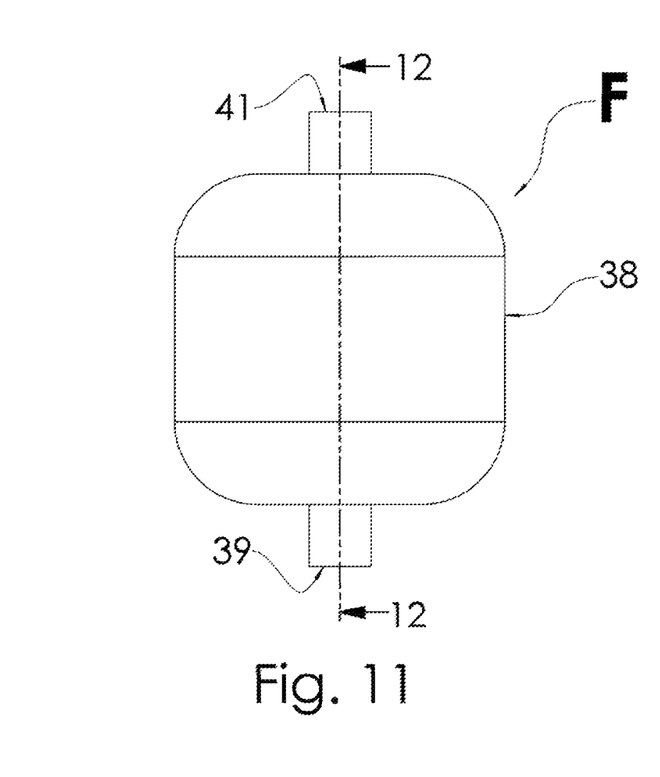
FIG. 11 is a planar side view illustrating another apparatus of the invention.
Figure 12:
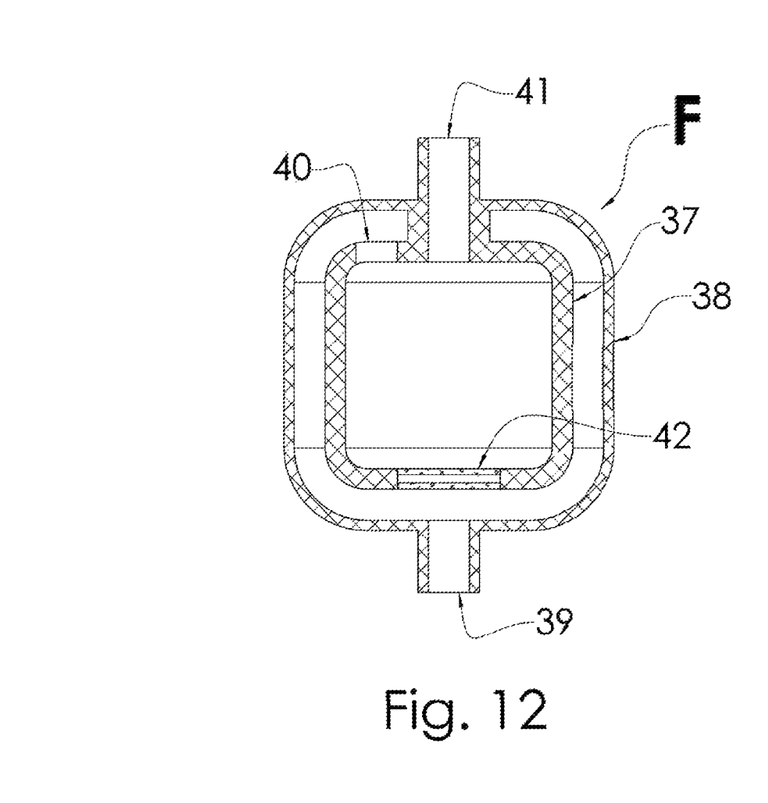
FIG. 12 is a section view of the apparatus of FIG. 11 taken along line 12-12.

Referring now to the embodiment shown in FIGS. 11 and 12, the irradiation apparatus F includes two three-dimensional chambers 37 and 38, each having an inlet port and an outlet port for the flow of a fluid into and out of the chambers. Irradiation chamber 37 has inlet port 40 for fluid flow into the chamber and outlet port 41 for fluid flow out of the chamber. Cooling chamber 38 has inlet port 39 for fluid flow into the chamber and outlet port 40 for fluid flow out of the chamber. Cooling chamber 38 and irradiation chamber 37 are in fluidic connection and in fluid communication, with port 40 functioning as the outlet port for the cooling chamber and the inlet port for the irradiation chamber. UV radiation planar source 42 is a micro plasma lamp that provides radiation to the interior of irradiation chamber 37 and to the interior of cooling chamber 38. The UV source is situated between the irradiation chamber and the cooling chamber and provides radiation to both chambers. Each side of the planar UV source serves as a portion of the sidewall of each chamber. The UV radiation source 42 has a quartz sleeve or optical window covering each of its sides to protect it from fluid in the irradiation chamber and cooling chamber. The UV radiation source is sealed between the windows such that the windows serve as a portion of the pressure vessel for the disinfection system and to segregate the UV radiation source from the fluid in the irradiation chamber.

In one embodiment, the irradiation chamber 37 is constructed from a material which principally reflects the UV radiation from the UV source and the cooling chamber 38 is constructed from a material which principally absorbs UV radiation. In another embodiment, both the irradiation chamber 37 and cooling chamber 38 are constructed from a material which principally reflects the UV radiation from the UV source. In another embodiment, both the irradiation chamber 37 and cooling chamber 38 are constructed from a material which principally absorbs the UV radiation from the UV source.

Figure 13:
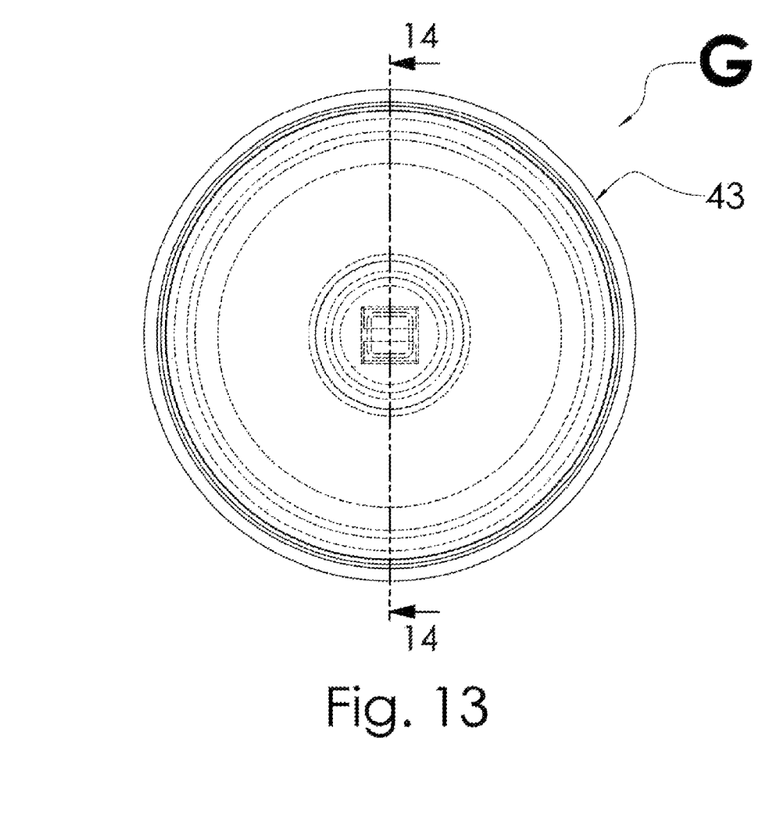
FIG. 13 is a planar side view illustrating another apparatus of the invention.
Figure 14:
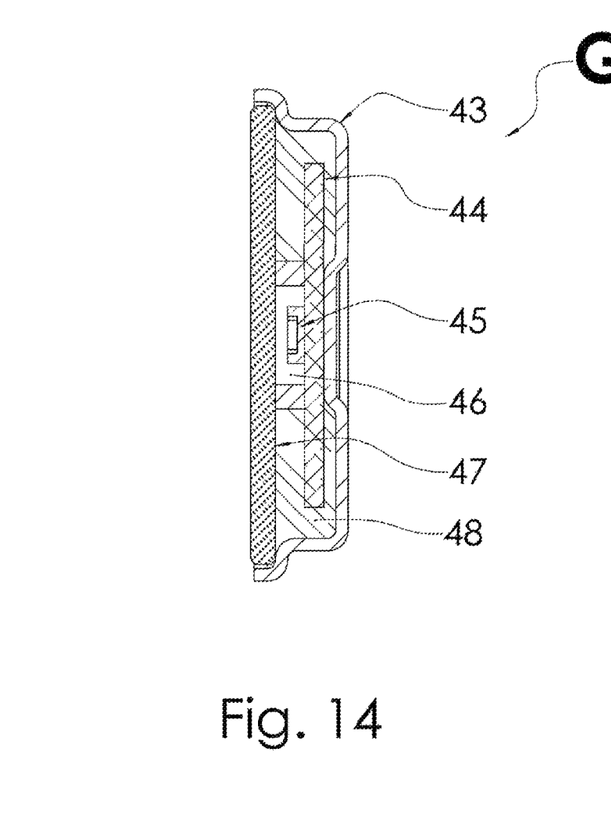
FIG. 14 is a section view of the apparatus of FIG. 13 taken along line 14-14.

In another embodiment of the invention, the UV source described herein may comprise a UV emitter, such as the UV emitter assembly G shown in FIGS. 13 and 14. UV emitter 45 is embedded inside an environmentally sealed housing which partially or completely encloses the UV emitter between a thermal transfer material or conductor 44, such as a metal core printed circuit board, and a UV transparent window 47. In another embodiment, the sealed housing comprises a principally UV transparent window, such as window 47, and a heatsink, such as a principally thermally conducting cup 43, that combine to form an enclosed volume in which one or more UV LEDs on a circuit board is located and which is in thermal connection to the cup. A potting compound 48 fills the void between the thermally conductive cup and the window, less a small keep out area 46 around the perimeter of the LEDs. In one embodiment, the thermally conductive cup is created by deformation of a single metal sheet. The thermally conductive cup may have one or more ports for electrical connection entry and/or exit and/or for the injection of a liquid potting compound. In another embodiment, the thermally conductive cup comprises at least one face intended principally for thermal transfer to/from the UV emitter.

In other embodiments of the invention, the optically transparent window is made of quartz or sapphire or a principally UV transparent polymer. The potting compound may principally retain the optically transparent window in the thermally conductive cup and serve as a structural component to the assembly. The UV emitter may comprise a UV radiation source mounted on a substrate with a control system further mounted on the substrate. The UV radiation source may comprise at least one of an LED, a plasma discharge source, or a solid-state phosphor emission device, or combinations thereof. The substrate may comprise a printed circuit board. The substrate may be designed to create an efficient thermal path between the UV radiation source and an external thermal reservoir. The substrate may provide a means of preventing contact between the potting compound and UV radiation source. The substrate may provide a means to fix relative positioning of the UV radiation source and the optically transparent window. A control system may comprise a constant-current source or a constant-current sink.

Although the invention is illustrated and described herein with reference to certain embodiments and examples thereof, it will be readily apparent to those skilled in the art that other embodiments and examples may perform similar functions and/or achieve like results. Likewise, it will be apparent that other applications of the disclosed technology are possible. All such equivalent embodiments, examples, and applications are within the spirit and scope of the invention and are intended to be covered by the following claims.

We claim:

1. An irradiation apparatus comprising:
    at least one irradiation chamber for a fluid containing a material to be irradiated, said chamber having at least one inlet port for fluid flow into the chamber and at least one outlet port for fluid flow out of the chamber;
    at least one cooling chamber having at least one inlet port for fluid flow into the chamber and at least one outlet port for fluid flow out of the chamber;
    one or more UV radiation sources coupled to the at least one irradiation chamber;
    a moisture seal and desiccant disposed adjacent to the one or more radiation sources; and
    at least one heat exchange mechanism thermally coupled to the one or more radiation sources and to the at least one cooling chamber;
    wherein at least a portion of the interior surface of the at least one cooling chamber comprises at least a portion of the exterior surface of the at least one irradiation chamber, and the at least one cooling chamber is in fluid communication with the at least one irradiation chamber.

2. The irradiation apparatus of claim 1, wherein the heat exchange mechanism comprises one or more of a thermoelectric cooling device, a vapor chamber, a heatsink, a heat dissipation structure, a fan, a thermal transfer material, a material thermally coupled to a fluid, and a cooling coating.

3. The irradiation apparatus of claim 2, wherein the heat exchange mechanism is a heatsink or a thermal transfer material, or combinations thereof.

4. The irradiation apparatus of claim 1, wherein the one or more UV radiation sources comprise one or more UV-C radiation sources, or a combination thereof.

5. The irradiation apparatus of claim 1, wherein the one or more UV radiation sources comprise a plurality of radiation sources arranged in an array.

6. The irradiation apparatus of claim 1, wherein one or more wavelengths of the one or more UV radiation sources are dynamically adjustable.

7. The irradiation apparatus of claim 1, wherein one or more wavelengths of the one or more UV radiation sources are selected based on an identification of a contaminant in the material to be irradiated.

8. The irradiation apparatus of claim 7, wherein the one or more UV radiation sources deliver one or more wavelengths to the material to be irradiated that induce fluorescence in the material to be irradiated thereby allowing for the identification of the contaminant in the material to be irradiated.

9. The irradiation apparatus of claim 1, wherein the one or more UV radiation sources deliver a combination of wavelengths to the material to be irradiated.

10. The irradiation apparatus of claim 1, wherein the one or more UV radiation sources comprise a micro plasma lamp.

11. An irradiation apparatus comprising:
    at least one irradiation chamber for a fluid containing a material to be irradiated, said chamber having at least one inlet port for fluid flow into the chamber and at least one outlet port for fluid flow out of the chamber;
    at least one cooling chamber having at least one inlet port for fluid flow into the chamber and at least one outlet port for fluid flow out of the chamber;
    one or more UV radiation sources coupled to the at least one irradiation chamber; and
    at least one heat exchange mechanism thermally coupled to the one or more radiation sources and to the at least one cooling chamber;
    wherein at least a portion of the interior surface of the at least one cooling chamber comprises at least a portion of the exterior surface of the at least one irradiation chamber, and the at least one cooling chamber is in fluid communication with the at least one irradiation chamber;
    said irradiation apparatus comprising a plurality of UV radiation sources and a plurality of irradiation chambers, each with at least one inlet and one outlet port, and all of the UV radiation sources are thermally coupled to a single cooling chamber.

12. The irradiation apparatus of claim 11, wherein the heat exchange mechanism comprises one or more of a thermoelectric cooling device, a vapor chamber, a heatsink, a heat dissipation structure, a fan, a thermal transfer material, a material thermally coupled to a fluid, and a cooling coating.

13. The irradiation apparatus of claim 12, wherein the heat exchange mechanism is a heatsink or a thermal transfer material, or combinations thereof.

14. The irradiation apparatus of claim 11, further comprising a moisture seal and desiccant disposed adjacent to the one or more radiation sources.

15. The irradiation apparatus of claim 11, wherein the one or more UV radiation sources comprise one or more UV-C radiation sources, or a combination thereof.

16. The irradiation apparatus of claim 11, wherein the one or more UV radiation sources comprise a plurality of radiation sources arranged in an array.

17. The irradiation apparatus of claim 11, wherein one or more wavelengths of the one or more UV radiation sources are dynamically adjustable.

18. The irradiation apparatus of claim 11, wherein one or more wavelengths of the one or more UV radiation sources are selected based on an identification of a contaminant in the material to be irradiated.

19. The irradiation apparatus of claim 18, wherein the one or more UV radiation sources deliver one or more wavelengths to the material to be irradiated that induce fluorescence in the material to be irradiated thereby allowing for the identification of the contaminant in the material to be irradiated.

20. The irradiation apparatus of claim 11, wherein the one or more UV radiation sources deliver a combination of wavelengths to the material to be irradiated.

21. The irradiation apparatus of claim 11, wherein the one or more UV radiation sources comprise a micro plasma lamp.

22. The irradiation apparatus of claim 11, wherein a portion of the radiation from the one or more radiation sources is transmitted to surfaces of one or more secondary chambers to inhibit biofilm formation on the surfaces.

23. An irradiation apparatus comprising:
- at least one irradiation chamber for a fluid containing a material to be irradiated, said chamber having at least one inlet port for fluid flow into the chamber and at least one outlet port for fluid flow out of the chamber;
- at least one cooling chamber having at least one inlet port for fluid flow into the chamber and at least one outlet port for fluid flow out of the chamber;
- one or more UV radiation sources coupled to the at least one irradiation chamber; and
- at least one heat exchange mechanism thermally coupled to the one or more radiation sources and to the at least one cooling chamber;
- wherein at least a portion of the interior surface of the at least one cooling chamber comprises at least a portion of the exterior surface of the at least one irradiation chamber, and the at least one cooling chamber is in fluid communication with the at least one irradiation chamber;
- and wherein a portion of the radiation from the one or more radiation sources is transmitted to surfaces of one or more secondary chambers to inhibit biofilm formation on the surfaces.

24. The irradiation apparatus of claim 23, wherein the heat exchange mechanism comprises one or more of a thermoelectric cooling device, a vapor chamber, a heatsink, a heat dissipation structure, a fan, a thermal transfer material, a material thermally coupled to a fluid, and a cooling coating.

25. The irradiation apparatus of claim 24, wherein the heat exchange mechanism is a heatsink or a thermal transfer material, or combinations thereof.

26. The irradiation apparatus of claim 23, further comprising a moisture seal and desiccant disposed adjacent to the one or more radiation sources.

27. The irradiation apparatus of claim 23, wherein the one or more UV radiation sources comprise one or more UV-C radiation sources, or a combination thereof.

28. The irradiation apparatus of claim 23, wherein the one or more UV radiation sources comprise a plurality of radiation sources arranged in an array.

29. The irradiation apparatus of claim 23, wherein one or more wavelengths of the one or more UV radiation sources are dynamically adjustable.

30. The irradiation apparatus of claim 23, wherein one or more wavelengths of the one or more UV radiation sources are selected based on an identification of a contaminant in the material to be irradiated.

31. The irradiation apparatus of claim 30, wherein the one or more UV radiation sources deliver one or more wavelengths to the material to be irradiated that induce fluorescence in the material to be irradiated thereby allowing for the identification of the contaminant in the material to be irradiated.

32. The irradiation apparatus of claim 23, wherein the one or more UV radiation sources deliver a combination of wavelengths to the material to be irradiated.

33. The irradiation apparatus of claim 23, wherein the one or more UV radiation sources comprise a micro plasma lamp.

34. The irradiation apparatus of claim 23, comprising a plurality of UV radiation sources and a plurality of irradiation chambers, each with at least one inlet and one outlet port, and all of the UV radiation sources are thermally coupled to a single cooling chamber.

* * * * *